(12) United States Patent
Uusivirta et al.

(10) Patent No.: US 7,752,894 B2
(45) Date of Patent: Jul. 13, 2010

(54) METHOD FOR MEASURING CONSISTENCY, CHOPPER STRUCTURE, AND CONSISTENCY METER

(75) Inventors: Lauri Uusivirta, Lempäälä (FI); Juhani Kangas, Kangasala (FI)

(73) Assignee: Metso Automation Oy, Helsinki (FI)

( * ) Notice: Subject to any disclaimer, the term of this patent is extended or adjusted under 35 U.S.C. 154(b) by 377 days.

(21) Appl. No.: 11/918,718

(22) PCT Filed: Apr. 27, 2006

(86) PCT No.: PCT/FI2006/050168

§ 371 (c)(1),
(2), (4) Date: Jan. 25, 2008

(87) PCT Pub. No.: WO2006/117434

PCT Pub. Date: Nov. 9, 2006

(65) Prior Publication Data

US 2009/0000357 A1    Jan. 1, 2009

(30) Foreign Application Priority Data

Apr. 29, 2005  (FI)  .................. 20055205

(51) Int. Cl.
*G01L 3/08*  (2006.01)
*G01N 11/14*  (2006.01)

(52) U.S. Cl. ................ 73/53.03; 73/54.33; 73/54.38; 73/862.324; 73/862.326; 73/862.328

(58) Field of Classification Search ................ 73/53.03, 73/54.33, 54.38, 862.191, 862.321, 862.324, 73/862.326, 862.328, 862.329
See application file for complete search history.

(56) References Cited

U.S. PATENT DOCUMENTS

| | | | |
|---|---|---|---|
| 3,518,003 A * | 6/1970 | Meyn | .......................... 356/367 |
| 3,572,086 A | 3/1971 | Johnston | |
| 4,590,806 A | 5/1986 | Lutton et al. | |
| 4,678,908 A * | 7/1987 | LaPlante | ................. 250/231.14 |
| 4,693,123 A * | 9/1987 | Bacardit | ................. 73/862.324 |
| 4,783,998 A * | 11/1988 | Sander | ........................ 73/660 |

(Continued)

FOREIGN PATENT DOCUMENTS

GB    2 206 205 A    12/1988

*Primary Examiner*—David A. Rogers
(74) *Attorney, Agent, or Firm*—Oliff & Berridge, PLC (57) ABSTRACT

The method measures consistency with a rotating consistency meter. The method comprises chopping with the teeth of a chopper structure optical radiation transmitted by an optical source to an optical detector while the shafts of the rotating consistency meter rotate. In addition, a chopper reference of the chopper structure chops optical radiation to form at least one reference pulse independent of the swivel between the shafts. The duration of each reference pulse is measured when measuring consistency. The change in the reference pulse is defined by comparing the duration of the measured reference pulse with the duration of the predefined reference pulse. The durations of the measuring pulses are corrected according to the change in the duration of the reference pulse.

29 Claims, 6 Drawing Sheets

U.S. PATENT DOCUMENTS

| | | | | |
|---|---|---|---|---|
| 4,809,557 A * | 3/1989 | Maurer et al. | ............ | 73/862.322 |
| 5,067,354 A * | 11/1991 | Kawai | .................... | 73/862.328 |
| 5,684,247 A | 11/1997 | Preikschat | | |
| 5,841,132 A * | 11/1998 | Horton et al. | ........... | 250/231.13 |
| 5,969,269 A * | 10/1999 | Munyon et al. | ......... | 73/862.328 |
| 6,285,024 B1 * | 9/2001 | Pinnock | ................. | 250/231.13 |
| 6,439,067 B1 * | 8/2002 | Goldman et al. | ........ | 73/862.333 |
| 6,541,760 B2 * | 4/2003 | Ohgoshi et al. | ......... | 250/231.13 |
| 6,679,126 B2 | 1/2004 | Dalton et al. | | |
| 6,800,843 B2 * | 10/2004 | Horton | ................... | 250/231.13 |
| 7,237,444 B2 * | 7/2007 | Berdichevsky et al. | . | 73/862.324 |
| 7,520,182 B2 * | 4/2009 | Takamura et al. | ....... | 73/862.321 |

* cited by examiner

METHOD FOR MEASURING CONSISTENCY, CHOPPER STRUCTURE, AND CONSISTENCY METER

FIELD

The invention relates to a method for measuring consistency, a chopper structure, and a consistency meter.

BACKGROUND

In process industry, the consistency of pulp can be measured using a rotating consistency transmitter that has two shafts within each other. A drive shaft is driven by a motor and a measuring shaft is flexibly mounted with bearings on the drive shaft, which makes an inter-shaft swivel possible. The swivel, which can also be indicated as an offset, may be a few degrees at most. There may be projections at the end of the measuring shaft, and the pulp to be measured tries to slow down the rotation of the projections with its consistency. The slowing down force depends on the consistency and causes a torque between the shafts, which tries to increase the offset between the flexibly bearing-mounted shafts. However, the shafts are electromagnetically coupled, and the offset between the shafts is kept constant by adjusting the amount of current supplied to the coils, whereby the magnetic forces compensate for the torque between the shafts.

The swivel between the shafts can be measured with an optocoupler that comprises an optical transmitter and receiver in such a manner that a toothed wheel rotating along with the shafts is attached to each shaft, and its teeth act as choppers of the beam between the optical transmitter and receiver, thus forming a pulsed signal to the receiver. When the shafts are in-phase, the teeth of the toothed wheels may converge. But when offset forms between the shafts, the teeth of the wheels shift correspondingly with respect to each other. This alters the length and ratio of the pulses of the optical signal. A measured pulse ratio is ordinarily further converted into a mean direct voltage. The offset between the shafts is thus directly proportional to the direct voltage that, in turn, is proportional to the pulse ratio.

There are, however, problems related to his type of measurement. The temperature, temperature changes and aging of measuring electronics affect the measuring results, and the error caused by them cannot be eliminated from the measurement. In addition, changes in the rotation speed of the shafts may cause errors.

BRIEF DESCRIPTION

It is an object of the invention to provide an improved method, chopper structure, and consistency meter.

This is achieved by a method for measuring consistency with a rotating consistency meter, the method comprising chopping a signal transmitted by a source to a receiver with the teeth of a chopper structure as the shafts of the rotating consistency meter rotate, while the lengths of measuring pulses detected by the receiver are proportional to the offset between the chopper teeth in different wheels in accordance with the swivel between the shafts. The method further comprises chopping the signal between the source and receiver with a chopper reference of the chopper structure to form at least one reference pulse independent of the swivel between the shafts, measuring the length of each reference pulse when measuring consistency, determining the change in the length of each reference pulse by comparing the length of the measured reference pulse with a predefined reference pulse length, and correcting the length of at least one measuring pulse according to the change in the length of said at least one reference pulse.

The invention also relates to a chopper structure for a rotating consistency meter that comprises a source, a receiver, and two shafts within each other and arranged to rotate and, when rotating, to swivel relative to each other; the chopper structure comprises two wheels that both comprise chopper teeth; one wheel of the chopper structure is to be fastened to one shaft of the rotating consistency meter, and the other wheel is to be fastened to the other shaft; the teeth of the chopper structure are intended to chop the signal transmitted by the source to the receiver while the shafts of the rotating consistency meter rotate, whereby the lengths of the measuring pulses detected at the receiver are proportional to the relative offset of the chopper teeth in different wheels in accordance with the swivel between the shafts. The chopper structure also comprises a chopper reference that is arranged by chopping the signal between the source and receiver to produce at least one reference pulse independent of the swivel between the shafts.

The invention further relates to a rotating consistency meter that comprises a chopper structure, a source, a receiver, and two shafts within each other and arranged to rotate and, when rotating, to swivel relative to each other; the chopper structure comprises two wheels that both comprise chopper teeth; one wheel of the chopper structure is to be fastened to one shaft of the rotating consistency meter, and the other wheel is to be fastened to the other shaft; the teeth of the chopper structure are intended to chop the signal transmitted by the source to the receiver while the shafts of the rotating consistency meter rotate, whereby the lengths of the measuring pulses detected at the receiver are proportional to the relative offset of the chopper teeth in different wheels in accordance with the swivel between the shafts. The chopper structure also comprises a chopper reference that is arranged by chopping the signal between the source and receiver to produce at least one reference pulse independent of the swivel between the shafts; and the consistency meter is arranged to determine the length of each reference pulse when measuring consistency; to determine the change in the length of the reference pulse by comparing the length of the reference pulse measured when measuring consistency with the duration of a predefined reference pulse; and to correct the length of at least one measuring pulse in accordance with the change in the at least one reference pulse length.

Preferred embodiments of the invention are disclosed in the dependent claims.

The method and system of the invention provide several advantages. Errors caused by temperature and the aging of electronics as well as those caused by changes in the rotation speed can be compensated.

LIST OF FIGURES

The invention will now be described in greater detail by means of preferred embodiments and with reference to the attached drawings, in which.

DESCRIPTION OF EMBODIMENTS

Figure 1A:
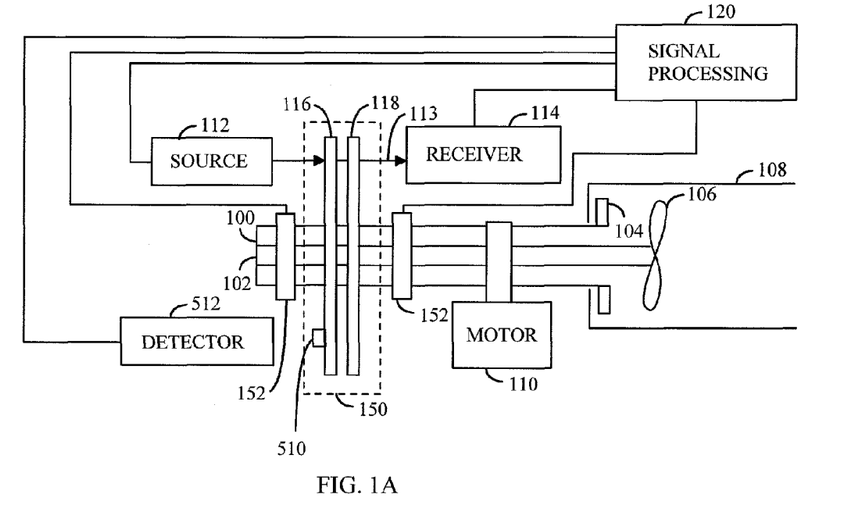
FIG. 1A shows a consistency transmitter.

FIG. 1A shows a rotating consistency transmitter capable of measuring the consistency of a suspension containing wood fibres, for instance. The measuring device comprises two shafts in such a manner that the inner shaft 102, also called a measuring shaft, is inside the outer shaft 100. There may be propeller-like structures 104, 106 at the end of both the outer shaft 100 and the inner shaft 102 to mix the suspension in the measuring chamber, for instance. A motor 110 may rotate the outer shaft 100, also called a drive shaft. Both shafts rotate in the same direction, and by means of a magnetic coupling provided by electromagnets 152, the swivel of the shafts 100, 102 can be kept constant in relation to each other, even though the cutting and friction forces dependent on the consistency of the measured suspension try to swivel the inner shaft 102 relative to the outer shaft 100. The swivel between the shafts 100, 102, which can also be called an offset, refers to the swivel of the shafts from a predefined initial position. Ordinarily, the shafts 100, 102 that are flexibly mounted with bearings to each other may swivel at most to a pre-defined degree, which may be a few degrees at most.

The swivel can be measured optically using an optical measuring device containing an optocoupler, for instance. The measuring device may comprise an optical source 112, an optical receiver 114, and a chopper structure 150. The chopper structure 150 may, in turn, comprise two similar wheels 116, 118 equipped with chopper teeth (not shown in FIG. 1). The outer shaft 100 may rotate the first of these wheels 116 and the inner shaft 102 may rotate the second wheel 118. As the wheels 116, 118 rotate along with the shafts 100, 102, the chopper teeth rotating act as choppers of the signal between the optical transmitter 112 and optical receiver 114 and form a pulsed signal to the receiver. Instead of the optical source, it is also possible to use some other source 112 capable of transmitting electromagnetic radiation, particle radiation, ultrasound or the like as a signal 113. The receiver 114 may, in turn, be a detector that is sensitive to the signal transmitted by the transmitter 112. When the shafts 100, 102 are irrotational, i.e. inphase, with respect to each other, the chopper teeth of the wheels may converge. However, when swivel forms between the shafts 100, 102, the chopper teeth of the wheels shift correspondingly relative to each other. This phase shift alters the pulse ratio of the optical signal. Thus, swivel is directly proportional to the pulse ratio with which a signal-processing unit 120 may control the electric current supplied to the electromagnets.

In consistency measurement, it is possible to utilise torque measurement in such a manner that with the electric current controlled by the signal processing unit 120 an electromagnetic field is formed in the coils of the electromagnets 152, the electromagnetic field having a countertorque corresponding to the torque of a measuring propeller. It is possible to try to keep the countertorque at a magnitude that the swivel between the drive shaft 100 and measuring shaft 102 remains zero or at another predefined value. The consistency can then be determined from the intensity of the electric current, as long as the correlation between the consistency and the torque is also known. The swivel can be measured with toothed wheels, because the phase shift between two wheels changes as a function of the swivel. The phase shift can be determined by measuring the pulse ratio with an optocoupler. However, the limited rise and fall time of the optocoupler electronics and their temperature dependency cause errors in the measurement, especially when the temperature or the rotation frequency of the wheels changes. The aging of the optocoupler electronics also causes errors.

Figure 1B:
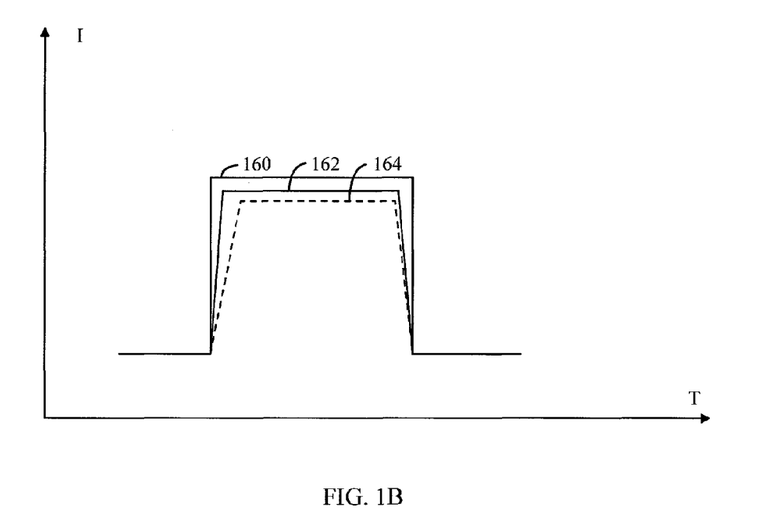
FIG. 1B shows a signal pulse arriving at a receiver and a signal pulse detected at two different temperatures.

FIG. 1B shows a detected signal at different temperatures. The vertical axis shows the intensity on a free scale and the horizontal axis shows the time on a free scale. The continuous line 160 shows the optical signal that the receiver has detected at two different temperatures. The line 162 shows the signal detected by the receiver at room temperature and the dashed line 164 shows the signal detected by the receiver at 70° C., for instance. FIG. 1B shows that the rise and fall times of the detected signal may be of different length and change in different ways when the temperature changes.

Figure 2A:
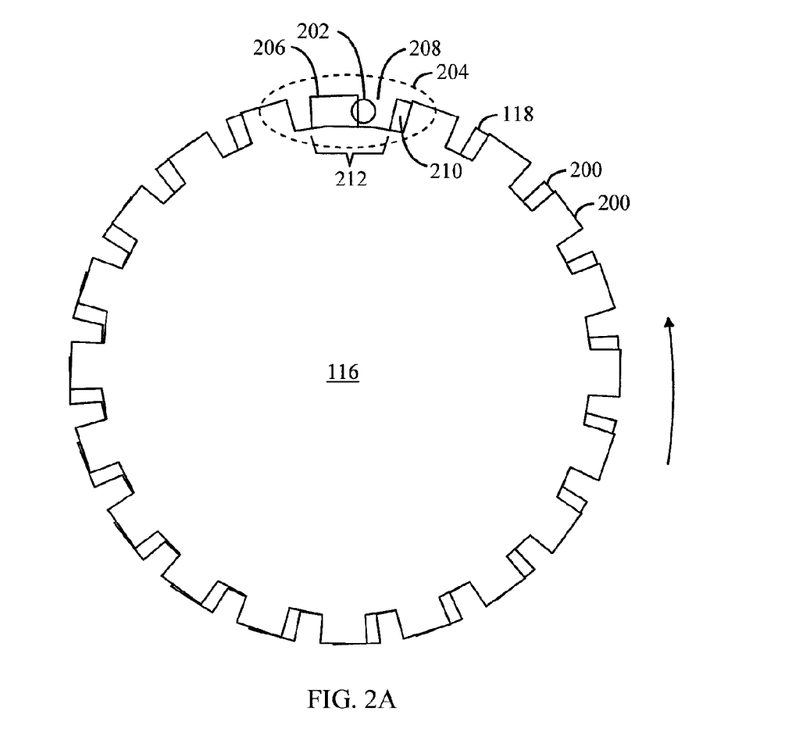
FIG. 2A shows a chopper structure, in which the chopper reference is formed by removing one chopper tooth.

Let us now examine more closely the chopper structure 150 by means of FIG. 2A. The chopper structure may comprise two wheels 116, 118 that both comprise at least one chopper tooth 200. The at least one chopper tooth may be on the outer rim of the wheel. Each wheel may have a desired number of chopper teeth 200 along the entire outer rim or on a part thereof. There may be approximately 100 chopper teeth, for instance. The width of each chopper tooth may be greater than the greatest allowed and predefined offset caused by swivel between the wheels. If this condition is met, the chopper teeth do not shift to the extent of their entire width with respect to each other.

One wheel of the chopper structure is to be fastened to one shaft of the rotating consistency meter and the other wheel is to be fastened to the other shaft.

Let us assume initially that there is no swivel between the shafts of the measuring device, the wheels 116, 118 are inphase, i.e. the wheel 118 is fully behind the wheel 116 so that the teeth of the wheel 118 cannot be seen from behind the wheel 116 in the presentation of FIG. 2A. FIG. 2A can be considered to present a situation in which the shafts of the measuring device have swiveled so that the teeth of the wheel 118 are not fully behind the teeth of the wheel 116. The chopper teeth 200 of the chopper structure are intended to chop the optical radiation 202 transmitted by the optical source to the optical detector as the shafts of the rotating consistency meter rotate. When the teeth 200 of the wheels 116, 118 shift relative to each other due to the swivel of the shafts, the durations of the pulses detected by the optical detector also change. In the case at hand, the pulses shorten, because the interlacing chopper teeth 200 narrow the optical clearance between the chopper teeth. The measured pulse time is also changed by the temperature and aging and the like of the measuring electronics, which cannot be eliminated from the measuring result without a reference measurement.

In the presented solution, the chopper structure comprises a chopper reference 204 arranged to provide at least one optical pulse of a pre-defined duration by chopping the optical radiation independent of the swivel between the shafts. The duration of this optical pulse acting as reference is predefined and known in a situation in which the rotation speed of the wheels 116, 118 is known. However, if the duration does differ from the predefined duration, the measuring result can be corrected.

In the case of FIG. 2A, the chopper reference 204 is implemented by removing one chopper tooth from the wheel 116. The optical pulse of predefined duration is then provided by a reference clearance 212. The width of the reference clearance 212 is the width of one chopper tooth 206 of the wheel 118 together with the clearance 208 of the chopper teeth between the teeth 206 and 210 of the wheel 118.

In the presented solution, it is also possible to remove more than one chopper tooth. It is then possible to remove several consecutive chopper teeth or several individual chopper teeth at different sides of the outer rim of the wheel. However, the operation is the same as in the case described above where only one chopper tooth is removed.

Figure 2B:
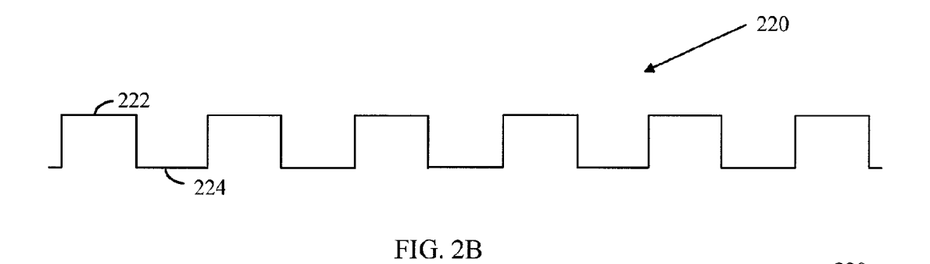
FIG. 2B shows pulsed optical radiation arriving at a detector.
Figure 2C:
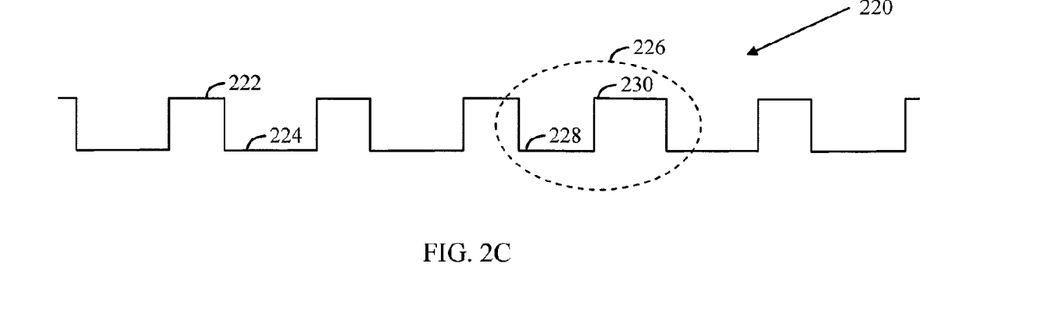
FIG. 2C shows pulsed optical radiation arriving at a detector.

Let us now use FIGS. 2B and 2C to examine the pulsed optical radiation 220 arriving at the detector when using the chopper structure of FIG. 2A and the assumption that without swivel the chopper teeth converge. In the case of FIG. 2B, the wheels 116, 118 overlap completely and, as the chopper teeth and their clearances are equal in this example, the duration of a forward pulse 222 is the same as the length of a reverse pulse 224. Both the forward pulse 222 and the reverse pulse 224 may act as the measuring pulse that can be used to indicate the swivel between the shafts. The length of the forward pulse (or reverse pulse) can then be compared with the total length of the forward and reverse pulses, i.e. the pulse ratio can be measured. The period of the measuring pulses can be thought to comprise the forward pulse 222 and reverse pulse 200. The length of such a measuring period can for instance be measured from the rising edges only, in which case the gap between two rising edges corresponds to a period. The length of the measuring period can alternatively be measure from falling edges only. Chopping a signal refers herein to the fact that during the forward pulse 222, optical radiation arrives at the detector and during the reverse pulse 224, radiation does not arrive at the detector or less radiation arrives at the detector than during the forward pulse 222. For this reason, the chopper teeth of the chopper structure cause regular level changes in the signal, and the detected intensity or power of the signal changes according to the chopping. The relative durations of the forward pulse 222 and reverse pulse 224 may also be of different lengths.

When the wheels have shifted relative to one another, as in FIG. 2A, the length of the reverse pulse 224 has increased, as shown in FIG. 2C. This also applies when the width of the chopper teeth differs from the clearances between the chopper teeth. The reverse pulse also lengthens in the case that the chopper teeth do not fully converge even though there is no swivel in the shafts, if the suspension to be measured rotates around the measuring device shafts in such a manner that the chopper teeth move more and more toward the clearances between the chopper teeth, i.e. the offset between the wheels increases. The cycle length related to measuring pulses does not change even though the lengths of the pulses change. In addition, even though the duration of the measuring pulses changes, the length of a reference pulse pair 226 formed by the forward pulse 228 and reverse pulse 230 used in the reference measurement does not change, if the rotation speed does not change, because the lengths of the forward pulse 228 and reverse pulse 230 are unchanged regardless of the swivel. The chopper tooth 206 of the wheel 118 and the clearance 208 between the chopper teeth, which is unchangeable, forms the reference pulse pair 226. When the rotating speed is unchanged, the durations of the reference pulse pair 226 and the forward pulse 230 and reverse pulse 228 are thus also unchanged. Correspondingly, even though the rotating speed changed, the durations of the forward pulse 230 and reverse pulse 228 acting as references would remain unchanged when corrected with the rotating speed.

When the wheels are fastened to measuring device shafts having no swivel in such a manner that the duration of the reverse pulse is not the shortest possible, i.e. there is a predefined offset between the wheels, the duration of the reverse pulse may shorten when the shafts rotate during measurement, if the measuring device shaft swivel caused by the suspension being measured decreases the offset between the wheels. One implementation could then be for instance that the duration of the reverse pulse is made as long as possible when there is no swivel between the measuring device shafts. In view of such a solution, it is possible to think that FIG. 2C shows the measuring signal without a sample causing the swivel and FIG. 2B shows the measuring signal when the swivel of the shafts is big.

Figure 3A:
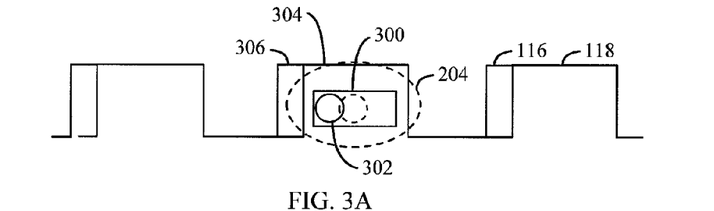
FIG. 3A shows a chopper reference made in a chopper tooth.

FIG. 3A shows a solution in which the chopper reference 204 is implemented as follows. In one chopper tooth 304 of the wheel 118, a swivel clearance 300 is made, whose width corresponds to the biggest possible offset between the wheels 116, 118 (i.e. the biggest swivel between the measuring device shafts). Swivel clearances 300 may also be made to more than one chopper tooth. The wheel 116, in turn, has an access clearance 302 in the chopper tooth 304 corresponding to the at least one chopper tooth 306 of the wheel 118 having a swivel clearance. The access clearance 302 may be without the measuring device shaft swivel at the location marked with a dashed line, but when the shafts of the measuring device rotate relative to each other, the access clearance 302 may shift to the marked location in the swivel clearance 300. Because neither the swivel between the shafts nor the relative offset of the wheels affects the size of the access clearance 302, the access clearance 302 provides to the detector a reference pulse whose duration remains unchanged when the rotation speed remains unchanged.

Figure 3B:
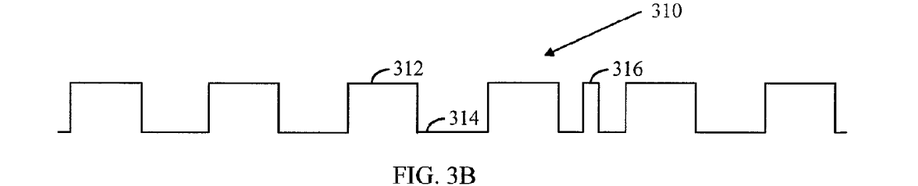
FIG. 3B shows pulsed optical radiation arriving at a detector.
Figure 3C:
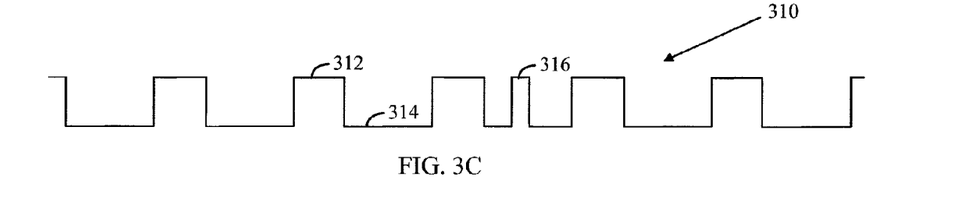
FIG. 3C shows pulsed optical radiation arriving at a detector.

FIGS. 3B and 3C show the pulse string provided by the chopper teeth and one access clearance to the detector. In both figures, the chopper teeth and clearances are shown having the same size, and the access clearance is assumed to be in the middle of a chopper tooth for the sake of simplicity. Other solutions are also possible. In the case of FIG. 3B, the optical signal 310 detected by the detector contains forward pulses 312 and reverse pulses 314 of the same length. It also shows the forward pulse 316 caused by the access clearance 302.

In FIG. 3C, the offset between the wheels 116, 118 has caused the reverse pulse 314 to become longer than the forward pulse 312. Regardless of the forward and reverse pulses and their ratios, the reference forward pulse 316 provided by the access clearance is, however, unchanged in duration while the rotation speed is unchanged.

Figure 4A:
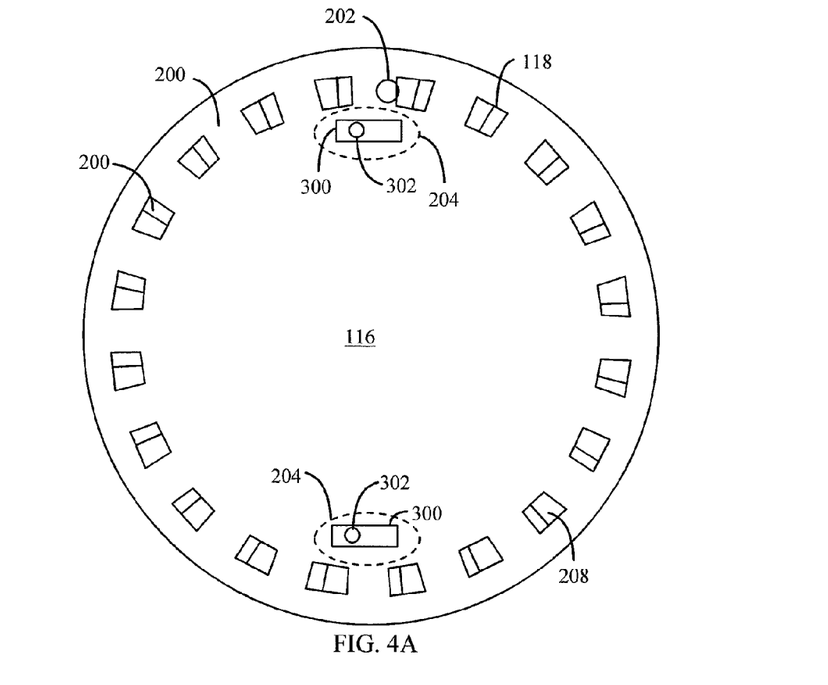
FIG. 4A shows a chopper reference made in a wheel.

FIG. 4A shows a chopper reference 204 that corresponds to FIG. 3A with the exception of having the swivel clearance 300 at some other location of the wheel instead of at the chopper tooth. FIG. 4A also shows two chopper references. Similarly, the access clearance 302 is located at some other location of the wheel than at the chopper tooth. Another difference is that the clearances between the chopper teeth now resemble windows, because the chopper teeth 200 are not protrusions on the outer rims of the wheels.

Figure 4B:
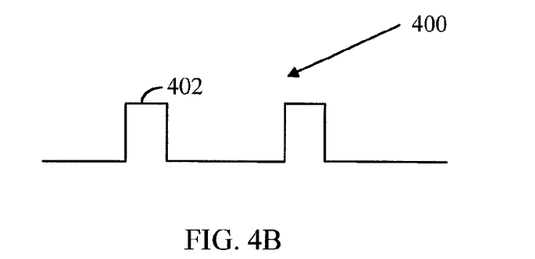
FIG. 4B shows pulsed optical radiation arriving at a detector.

If the reference pulse is detected with a specific detector, the reference signal 400 can be shown as in FIG. 4B. The detector then receives reference pulses 402 whose durations are influenced by the size of the access clearance 302 and the rotation speed of the wheel. Because the size of the access clearance is constant, the duration of the reference pulse remains unchanged when the rotation speed remains unchanged.

Figure 5A:
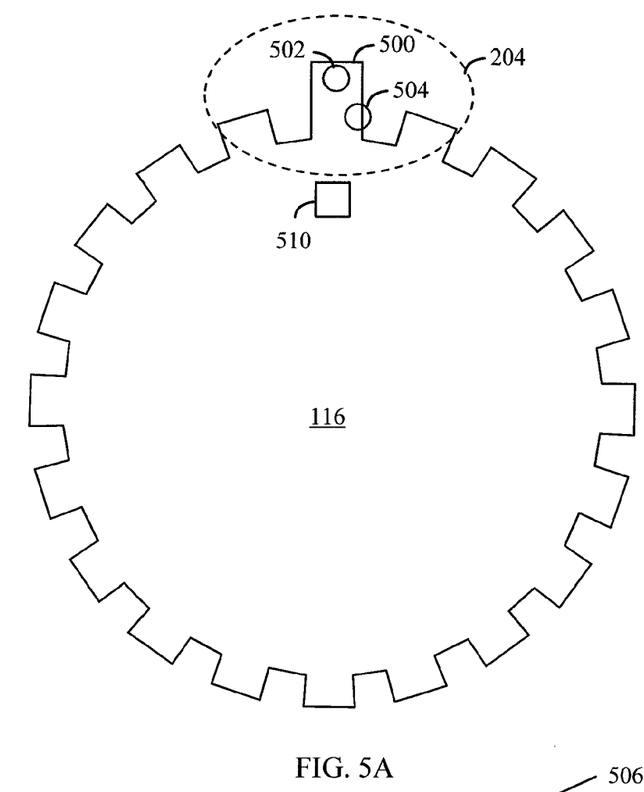
FIG. 5A shows a reference structure comprising a chopper tooth.

FIG. 5A shows a solution in which an optical pulse intended as reference is formed with a chopper tooth 500 that is longer than the other chopper teeth. In addition to one long chopper tooth 500 or instead of it, there may be several extended chopper teeth consecutively, at regular intervals, or at irregular intervals. An optical beam 502 measuring the reference only hits the extended chopper tooth, whereas the relative offset of the chopper teeth is measured with an optical beam 504 that hits all the chopper teeth.

Figure 5B:
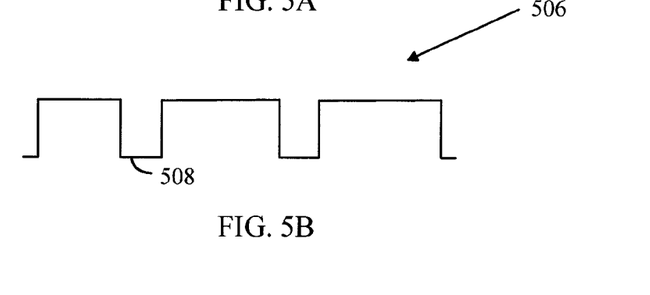
FIG. 5B shows pulsed optical radiation arriving at a reference detector.

If the reference pulse is detected with a specific detector, the reference signal 506 can be shown as in FIG. 5B. The detector then receives reference pulses 508 whose durations are influenced by the width of the chopper tooth and the rotation speed of the wheel. Because the width of the chopper tooth is constant, the duration of the reference pulse 508 remains unchanged when the rotation speed remains unchanged. In this solution, the pulses acting as reference pulses are reverse pulses.

FIGS. 5A and 1 show one solution for measuring the rotation speed of the wheel. A marker component 510 can be fastened to the wheel 116 (or 118), and a marker detector 512 detects its movement. The marker element 510 may be a magnet that passes the marker detector 512 during each rotation of the wheel. The passing marker element 510 causes an impulse in the marker detector 512, and the interval between consecutive impulses is the duration of one revolution. The marker detector 512 converts the impulses caused by the marker element 510 into an electric signal and feeds the signal to the signal processing unit 120 that uses it to determine the revolution time $t_k$ and rotation frequency $f_s$ of the wheel. There may also be several marker elements and they may operate in other ways than magnetically. The rotation speed of the wheel can also be determined by means of the duration of a period formed by two or more measuring pulses. The rotation speed can then be determined on the basis of one period that is measured from a rising edge to a rising edge or a falling edge to a falling edge. The widths of the chopper tooth and the clearance between chopper teeth need to be known for this. Correspondingly, the rotation speed can be determined from more than one period. The rotation speed can also be determined by measuring the time required for one revolution by determining the total time of all pulses (reverse and forward pulses). The number of chopper teeth then need to be known so as to take the correct number of pulses into consideration in the measurement. The rotation speed of the wheel can also be determined by means of the chopper reference structure 204. The time required for one revolution can then be measured as the time between the consecutive detections of one chopper structure, for instance.

Figure 6:
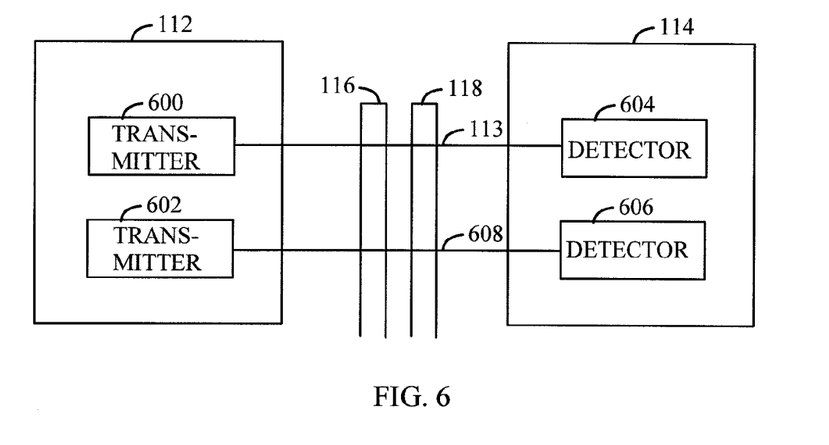
FIG. 6 shows an optical source and an optical receiver that both have two pieces.

The optical source 112 shown in FIG. 1 may comprise several transmitter units instead of one, and the optical receiver 114 may comprise several receiver units instead of one. FIG. 6 shows two transmitter units 600, 602 and two detectors 604, 606. From the transmitter unit 600 used in measuring swivel, the optical beam 113 may propagate through the chopper structure 150 to the detector 604 used in measuring swivel, and from the reference transmitter unit 602, the optical beam 608 may propagate through the chopper structure 150 to the second reference detector 606. This solution is suited for the cases in at least FIGS. 4A to 5B.

Figure 7:
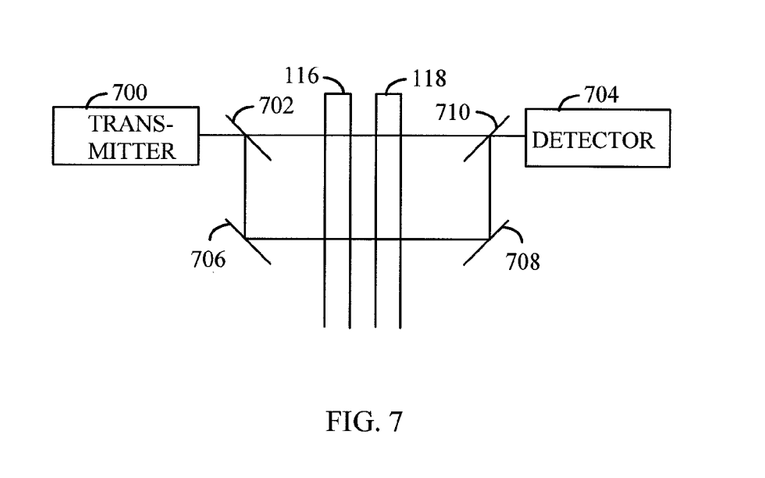
FIG. 7 shows an optocoupler, in which an optical beam is divided into two different paths.

FIG. 7 shows a solution in which one transmitter unit 700 transmits one optical beam toward the chopper structure 150, but before the chopper structure 1150, the beam is split with a beam splitter 702 into two beams. The first beam may propagate directly through the chopper structure 150 to a detector 704, whereas the second beam can be directed by means of a first reflector element 706 to the chopper structure 150, after which the beam can be combined by means of a second reflector element 708 and a second beam splitter 710 with the first beam for propagating to the detector 704.

Figure 8:
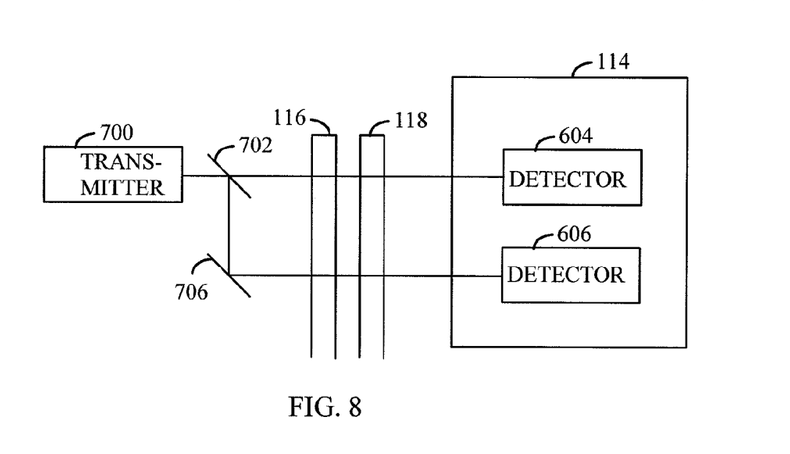
FIG. 8 shows an optocoupler in which an optical beam is divided into two different paths and detected at two different receiver units.

In FIG. 8, the beam from the transmitter unit 112 is split into two beams with the beam splitter 702. The first beam may propagate through the chopper structure 150 to the first detector 604. The second beam may propagate through the chopper structure 150 by means of the reflector element 706 to the reference detector 606. The reflector elements may be mirrors or prisms.

FIGS. 6 and 8 may correspond to the solution in FIG. 4A or 5A. In FIGS. 6 to 8, the first beam may be a beam measuring the offset of the chopper teeth with respect to each other, and the second beam may be a beam measuring the reference, or the second beam may be a beam measuring the offset of the chopper teeth with respect to each other, and the first beam a beam measuring the reference.

Let us now examine the measuring method on the basis of the presented hardware description. The N chopper teeth 200 that affect the operation of the optocoupler form to the receiver pulses whose pulse ratio changes according to the change in the relative position of the teeth. Let us mark the forward pulse with HI and the reverse pulse with LO. At least one reference structure forms a pulse of predefined length regardless of the relationship between the chopper teeth. The length of this reference pulse thus changes only due to a temperature change and the aging of the electronic parts of the measuring device when the rotation speed of the wheel is constant.

A rotation parameter of the rotating consistency meter, which can be the rotation frequency or rotation speed, can be determined from the duration of the pulses in one revolution. The revolution time, i.e. the duration of a revolution is the sum of the duration of N forward pulses and N reverse pulses, for instance. The rotation frequency can be measured in predefined conditions (test jig) at the factory, for instance. The rotation frequency $f_s$ is then:

$$F_s = 1/t_k,$$

wherein $t_k$ is the revolution time of the wheels. The revolution time can be defined by means of reference pulses or a separate revolution measurement, as described in connection with FIG. 5A. The rotation frequency can also be defined by calculation or simply assumed. The rotation frequency of a shaft may for instance be approximately 6.5 Hz when the frequency of the electric network is 50 Hz, and approximately 7.7 when the frequency of the electric network is 60 Hz. If the rotation frequency is in a range in which the device works normally, the device is operational.

When installing the rotating consistency transmitter to its actual measuring site, the rotation speed can be compared with one measured in predefined conditions. The frequency correction $f_k$ can then be calculated with respect to the predefined conditions as follows:

$$f_k = f_s/f_m,$$

wherein $f_m$ is the rotation frequency measured at the actual measuring site. In standard conditions, the alternating current frequency of the electric network may be 50 Hz, for instance. The frequency of the electric network may affect the rotation speed of shafts driven with an electric motor. At the actual measuring site, the alternating current frequency of the electric network may be 60 Hz, for instance, in which case the shafts of the measuring device may rotate at a different speed than in the standard conditions.

So as to be able to utilise the duration of the reference pulse in correcting errors, it must be found among the pulses of the last revolution. Let us first examine the reference pulse pair 226 formed by the reference structure of FIG. 2A. The forward and reverse sections of the reference pulse can be found by examining the last N pulses and finding the longest forward section 230 or shortest reverse section of the pulses. Let us mark the duration of the forward section of the found reference pulse with REFHI and the duration of the reverse section 228 of the reference pulse with REFLO. Let us then mark the sum of the forward sections of all pulses (including the reference pulse) in the revolution by SUMHI and the corresponding sum of the reverse sections with SUMLO.

The duration $t_r$ of the signal provided by other than the reference teeth in the revolution is the sum of the forward and reverse pulse sections:

$$t_r = (\text{SUMHI} - \text{REFHI}) + (\text{SUMLO} - \text{REFLO}).$$

When measuring consistency in actual measuring conditions, the duration of the forward section of the reference pulse may change in comparison with the (rotation speed corrected) standard conditions as follows:

$$\Delta \text{REFHI} = \text{REFHI} - f_k * \text{REFHI}s,$$

wherein $\Delta$REFHI is the change and REFHIs is the REFHI measured in standard conditions. $\Delta$REFHI obtains the value 0, if there is no change due to temperature, aging, or the like.

The duration of all pulses changes in the same manner as that of the reference pulse. When pulse ratio is calculated, said pulse duration change multiplied by the number of normal teeth must be deducted from the sum of the durations of the pulses formed by all normal teeth. The corrected pulse ratio $c_f$ is then:

$$c_f = \frac{(\text{SUMHI} - \text{REFHI}) - \Delta \text{REFHI} \cdot N}{t_r},$$

wherein $c_f$ is the corrected pulse ratio. In this equation, the term $\Delta$REFHI·N takes into account both the rotation speed and the changes in the length of the pulse due to the temperature, temperature changes and ageing or the like.

A change in the duration of the reference pulse $\Delta$REFHI is a distortion to the predefined conditions. The length of the measuring pulses is also correspondingly distorted and needs to be corrected. The distortion can then be deducted from the length of the measuring pulses. The above correction is done by utilising the forward section (HI, REFHI, REFHIs, SUMHI) of the pulsed signal. The correction can also be done by using the reverse sections (LO, REFLO, REFLOs, SUMLO) of the pulsed signal instead of the forward sections.

In the cases of FIGS. 3A to 5B, the processing can progress correspondingly as follows. When the rotation speed or revolution time is defined both in standard conditions and at the actual measuring site, it is possible to calculate, how much the duration REF of the reference pulse has changed in comparison with the (rotation speed corrected) standard conditions:

$$\Delta \text{REF} = \text{REF} - f_k * \text{REF}s,$$

wherein $\Delta$REF is the change and REFs is the REF measured in standard conditions. The change $\Delta$REF obtains the value 0, if the rotation speed has not changed and there are no other changes.

The pulse ratio $c_f$ can now be formed as follows:

$$c_f = \frac{\text{PULSE} - \Delta REF}{\text{PULSE}},$$

wherein PULSE is the duration of the measured pulse and PULSE=HI+LO.

The result can be averaged by measuring the pulses of a full revolution, for instance. The sum SUMPULSE of the durations of the forward and reverse pulse sections of a full revolution is:

$$\text{SUMPULSE} = \text{SUMHI} + \text{SUMLO}.$$

In this case, the sum $t_r$ of the duration of the pulses is at least approximately equal to the revolution time $t_k$, in which case $t_r$ can be replaced with the revolution time $t_k$ in the equation below. The corrected pulse ratio $c_f$ is then:

$$c_f = \frac{SUMPULSE - \Delta REF \cdot N}{t_r},$$

wherein SUMPULSE is the duration of the forward or reverse pulses to be measured, $c_f$ is the corrected pulse ratio, and N is the number of the forward or reverse pulses to be measured.

Figure 9:
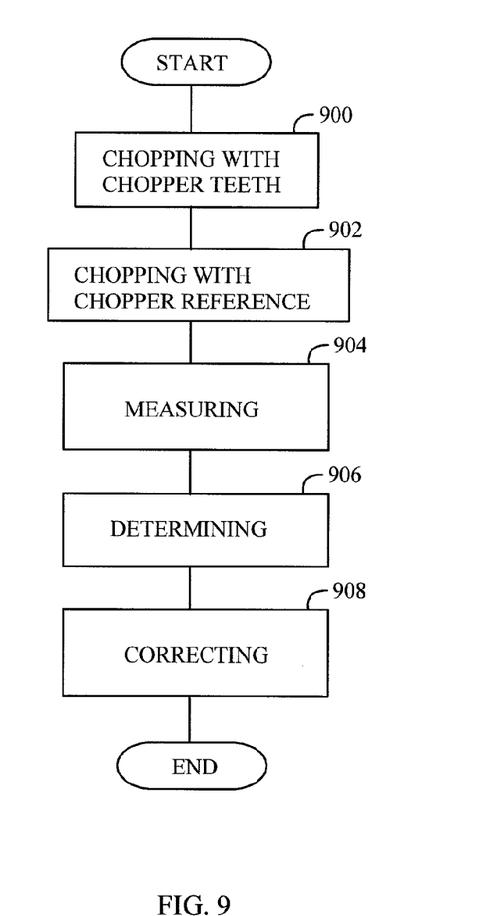
FIG. 9 is a flow chart of the method.

FIG. 9 shows a flow chart of the method. In step 900, the signal between the transmitter and receiver is chopped and measuring pulses are formed. In step 902, the signal between the transmitter and receiver is chopped and reference pulses are formed. In step 904, the length of at least one reference pulse is measured. In step 906, the change in the length of the reference pulse is determined. In step 908, the length of at least one measuring pulse is corrected for consistency measurement.

Even though the invention is above described with reference to examples according to the attached drawings, it is apparent that the invention is not limited thereto but may be varied in many ways within the scope of the attached claims.

The invention claimed is:

1. A method for measuring consistency with a rotating consistency meter, the method comprising chopping a signal transmitted by a source to a receiver with the teeth of a chopper structure as the shafts of the rotating consistency meter rotate, while the lengths of measuring pulses detected by the receiver are proportional to the offset between the chopper teeth in different wheels in accordance with the swivel between the shafts further comprising chopping the signal between the source and receiver with a chopper reference of the chopper structure to form at least one reference pulse independent of the swivel between the shafts, measuring the length of each reference pulse when measuring consistency, determining the change in the length of each reference pulse by comparing the length of the measured reference pulse with a predefined reference pulse length, and correcting the length of at least one measuring pulse according to the change in the length of said at least one reference pulse.

2. A method as claimed in claim 1, further comprising measuring each reference pulse by using a separate optical reference transmitter unit and optical reference detector as the chopper reference of the chopper structure chops the optical radiation transmitted by the reference source to the reference detector.

3. A method as claimed in claim 1, wherein for the purpose of determining the change in the length of the reference pulse, the length of a predefined reference pulse is formed by determining the duration of the reference pulse in predefined conditions.

4. A method as claimed in claim 1, further comprising using a computational predefined length as the predefined reference pulse length.

5. A method as claimed in claim 1, further comprising
defining by means of the chopper reference a rotation parameter of the wheels that represents the rotation frequency or speed of the wheels,
comparing the rotation parameter with a predefined rotation parameter, and
correcting the lengths of measuring pulses according to the comparison of the rotation parameter and the predefined rotation parameter.

6. A method as claimed in claim 1, further comprising
defining by means of the measuring pulses a rotation parameter of the wheels that represents the rotation frequency or speed of the wheels,
comparing the rotation parameter with a predefined rotation parameter, and
correcting the lengths of the measuring pulses according to the comparison of the rotation parameter and the predefined rotation parameter.

7. A method as claimed in claim 1, further comprising measuring the predefined rotation parameter in predefined conditions.

8. A method as claimed in claim 1, further comprising using a computational rotation parameter as the predefined rotation parameter.

9. A method as claimed in claim 1, further comprising measuring the rotation parameter by means of a separate marker detector and a separate marker element in at least one wheel,
comparing the rotation parameter measured in actual consistency measuring conditions with the predefined rotation parameter,
correcting the lengths of the measuring pulses measured in actual consistency measuring conditions according to the comparison of the measured rotation parameter and the predefined rotation parameter.

10. A chopper structure for a rotating consistency meter that comprises a source, a receiver, and two shafts within each other and arranged to rotate and, when rotating, to swivel relative to each other;
the chopper structure comprises two wheels that both comprise chopper teeth;
one wheel of the chopper structure is to be fastened to one shaft of the rotating consistency meter, and the other wheel is to be fastened to the other shaft;
the teeth of the chopper structure are intended to chop the signal transmitted by the source to the receiver while the shafts of the rotating consistency meter rotate, whereby the lengths of the measuring pulses detected at the receiver are proportional to the relative offset of the chopper teeth in different wheels in accordance with the swivel between the shafts, wherein the chopper structure also comprises a chopper reference that is arranged by chopping the signal between the source and receiver to produce at least one reference pulse independent of the swivel between the shafts.

11. A chopper structure as claimed in claim 10, wherein when the source comprises a separate reference source unit and the receiver comprises a reference detector, the chopper reference of the chopper structure is arranged to chop the signal transmitted by the reference source to the reference detector.

12. A chopper structure as claimed in claim 10, wherein the chopper reference comprises in one wheel a reference clearance of the chopper teeth that corresponds to one chopper tooth width and two chopper teeth clearances, whereby the at least one chopper tooth and chopper tooth clearance at the reference clearance of the second wheel serve as the generators of a reference pulse.

13. A chopper structure as claimed in claim 10, wherein the chopper reference comprises in at least one chopper tooth of one wheel a swivel clearance and in at least one chopper tooth of the other wheel a corresponding access clearance that is arranged to produce a reference pulse.

14. A chopper structure as claimed in claim 10, wherein the chopper reference comprises in one wheel at least one swivel clearance and in the other wheel a corresponding access clearance that is arranged to produce a reference pulse.

15. A chopper structure as claimed in claim 10, wherein the chopper reference comprises in one wheel at least one chopper tooth that is longer than the other chopper teeth and arranged to produce a reference pulse.

16. A chopper structure as claimed in claim 10, wherein at least one of the wheels comprises a marker element with which the consistency meter defines a rotation parameter of the wheel.

17. A rotating consistency meter that comprises a chopper structure, source, receiver and two shafts within each other and arranged to rotate and, when rotating, to swivel relative t to each other,
the chopper structure comprises two wheels that both comprise chopper teeth;
one wheel of the chopper structure is to be fastened to one shaft of the rotating consistency meter, and the other wheel is to be fastened to the other shaft;
the teeth of the chopper structure are intended to chop the signal transmitted by the source to the receiver while the shafts of the rotating consistency meter rotate, whereby the lengths of the measuring pulses detected at the receiver are proportional to the relative offset of the chopper teeth in different wheels in accordance with the swivel between the shafts, wherein the chopper structure also comprises a chopper reference that is arranged by chopping the signal between the source and receiver to produce at least one reference pulse independent of the swivel between the shafts; and the consistency meter is arranged to
define the length of each reference pulse when measuring consistency;
define the change in the length of the reference pulse by comparing the length of the reference pulse measured when measuring consistency with the duration of the predefined reference pulse; and
correct the length of at least one measuring pulse according to the change in the length of the at least one reference pulse.

18. A consistency meter as claimed in claim 17, wherein the source comprises a reference source, and the receiver comprises a reference detector, and the chopper reference of the chopper structure is arranged to chop the signal transmitted by the reference source to the reference detector.

19. A consistency meter as claimed in claim 17, wherein the chopper reference comprises in one wheel a reference clearance of the chopper teeth that corresponds to one chopper tooth width and two chopper teeth clearances, whereby the at least one chopper tooth and chopper tooth clearance at the reference clearance of the second wheel serve as the generators of a reference pulse.

20. A consistency meter as claimed in claim 17, wherein the chopper reference comprises in at least one chopper tooth of one wheel a swivel clearance and in at least one corresponding chopper tooth of the other wheel an access clearance that is arranged to produce a reference pulse.

21. A consistency meter as claimed in claim 17, wherein the chopper reference comprises in one wheel at least one swivel clearance and in the other wheel at least one corresponding access clearance that is arranged to produce a reference pulse.

22. A consistency meter as claimed in claim 17, wherein the chopper reference comprises in one wheel at least one chopper tooth that is longer than the other chopper teeth and arranged to produce a reference pulse.

23. A consistency meter as claimed in claim 17, wherein the consistency meter is arranged to define the duration of at least one reference pulse in predefined conditions so as to form the duration of a predefined reference pulse.

24. A consistency meter as claimed in claim 17, wherein the predefined length of the reference pulse is formed by calculation.

25. A consistency meter as claimed in claim 17, wherein the consistency meter is arranged to
define by means of the chopper reference a rotation parameter of the wheels that represents the rotation frequency or speed of the wheels,
compare the measured rotation parameter with a predefined rotation parameter, and
correct the durations of the measured measuring pulses according to the comparison of the measured rotation parameter and the predefined rotation parameter.

26. A consistency meter as claimed in claim 17, wherein the consistency meter is arranged to
define by means of the measuring pulses a rotation parameter of the wheels that represents the rotation frequency or speed of the wheels,
compare the rotation parameter with a predefined rotation parameter, and
correct the lengths of the measuring pulses according to the comparison of the rotation parameter and the predefined rotation parameter.

27. A consistency meter as claimed in claim 17, wherein the consistency meter is arranged to measure the predefined rotation parameter in predefined conditions.

28. A consistency meter as claimed in claim 17, wherein the predefined rotation parameter is formed by calculation.

29. A consistency meter as claimed in claim 17, wherein at least one of the wheels comprises a marker element and the consistency meter comprises a marker detector that is arranged to detect the movement of the marker element for the purpose of defining the rotation parameter.

* * * * *